United States Patent [19]
Wang

[11] Patent Number: 5,068,396
[45] Date of Patent: Nov. 26, 1991

[54] ARYLCYCLOBUTENE CARBOXYLATE ESTERS

[75] Inventor: Pen-Chung Wang, Houston, Tex.

[73] Assignee: Shell Oil Company, Houston, Tex.

[21] Appl. No.: 370,507

[22] Filed: Jun. 23, 1989

[51] Int. Cl.$^5$ .............................................. C07C 69/76
[52] U.S. Cl. .................................................... 560/102
[58] Field of Search ......................................... 560/102

[56] References Cited

U.S. PATENT DOCUMENTS 4,540,763  9/1985  Kirchhoff ............................ 526/281

Primary Examiner—Paul J. Killos

[57] ABSTRACT

Novel 1-arylcyclobutenecarboxylate ester derivatives of N-glycidylamine compounds are self-curing thermosetting resins. The cured products obtained by applying heat to the ester derivatives, in the presence of or in the absence of added curing agent, are crosslinked insoluble solid materials having useful properties.

8 Claims, No Drawings

ARYLCYCLOBUTENE CARBOXYLATE ESTERS

FIELD OF THE INVENTION

This invention relates to a novel class of ester derivatives of nitrogen-containing compounds having two or more glycidyl substituents bound to nitrogen atoms. More particularly, the invention relates to arylcyclobutenecarboxylate derivatives of such N-glycidyl compounds, wherein the arylcyclobutene ring system is connected to the remainder of the molecule by a carboxy group substituted on a carbon atom of a cyclobutene ring, and to the cured products obtained by heating the derivatives.

BACKGROUND OF THE INVENTION

The curing of monomeric materials to produce thermoset resins is well known in the art. In general, the polymerizable or curable monomers have at least one and customarily more than one active group which serves as the reactive site for a curing or crosslinking polymerization to produce the thermoset resins which are typically highly crosslinked. The curing or crosslinking of many if not most thermosetting resins, for example, the curing of epoxy resins, requires the use of a curing agent, whether catalytic or stoichiometric, to cause a curing or crosslinking reaction to take place at an acceptable rate. Certain other monomers cure in the absence of added curing agent but only upon the application of high intensity energy, e.g., ultraviolet (UV) light. Even in the presence of a curing agent the rate of crosslinking is often unduly slow and the addition of an accelerator is generally required to obtain a sufficiently rapid curing.

There are some monomers in which the active sites are such that no added curing agent is required and the monomers cure upon application of heat. Such monomers are termed "self-curing". One class of these self-curing monomers includes within the molecular structure one or more moieties of an arylcyclobutene, particularly a benzocyclobutene. These monomers are suitably cured by reaction with, or in the presence of, a conventional curing agent but also self-cure upon heating in the absence of a curing agent. Without wishing to be bound by any particular theory, it appears probable that upon application of heart the cyclobutene ring undergoes ring opening to produce active intermediates which crosslink by undergoing reaction with adjacent molecules. The resulting cured thermoset resins have properties of rigidity and strength.

A series of U.S. patents to Kirchhoff, illustrated by U.S. Pat. No. 4,540,763, describes the production and curing of a large number of benzocyclobutene derivatives, including ethers of bisphenols including 2,2-di(4-hydroxyphenyl)propane, wherein the linking group connecting the benzocyclobutene moiety to the remainder of the molecule is attached directly to the six-membered ring of the benzocyclobutene moiety. Such monomers are said to be self-curing. In copending U.S. application Ser. No. 349,546, filed May 9, 1989, there is described and claimed a class of benzocyclobutene-type ethers of bisphenols wherein the benzocyclobutene moiety is attached to the remainder of the molecule through a somewhat different link but nevertheless a link attached to the six-membered ring of the benzocyclobutene. These derivatives are also self-curing.

A somewhat different type of benzocyclobutene-type compound is illustrated by copending U.S. patent application Ser. No. 364,275 filed June 12, 1989 now U.S. Pat. No. 4,954,583 and Ser. No. 364,276, filed June 12, 1989 now U.S. Pat. No. 4,954,584 which are directed to esters of glycidyl ethers of bisphenols such as 2,2-di(4-hydroxyphenyl)propane wherein the ester moiety connecting the benzocyclobutene-type ring system to the remainder of the molecule is attached to a carbon atom of a four-membered ring. It would be of advantage, however, to produce other types of such esters which cure in the presence of or in the absence of added curing agent to produce thermoset resins having useful properties.

SUMMARY OF THE INVENTION

This invention provides a novel class of arylcyclobutenecarboxylate ester derivatives of N-glycidyl compounds having at least two glycidyl moieties attached to nitrogen atoms. More particularly, the invention provides such arylcyclobutenecarboxylates wherein the carboxy linking group is attached to a four-membered ring of the arylcyclobutene ring system. The invention also relates to a process for the production of such esters and to the crosslinked, insoluble cured products obtained by heating the ester derivatives.

DESCRIPTION OF THE INVENTION

The arylcyclobutenecarboxylate portion of the novel monomeric esters of the invention is provided by a 1-arylcyclobutenecarboxylic acid which reacts to open the oxirane ring of the glycidyl groups and produce 1-arylcyclobutenecarboxylate esters at the terminal or gamma carbon atom of the former glycidyl group. The arylcyclobutenecarboxylic acid is a compound of the formula $A-CO_2H$ wherein the carboxyl group is substituted on a carbon atom of a four-membered cyclobutene ring. The arylcyclobutene moiety, A, is an aromatic ring system of up to 4 aromatic rings and up to 30 carbon atoms inclusive which contains at least one cyclobutene ring fused to an aromatic ring. Suitable aromatic ring systems are illustrated by the single aromatic ring system compound benzene, the fused ring system compounds naphthalene, anthracene and phenanthrene, the directly-joined aromatic ring system compounds biphenyl and 1-phenylnaphthalene and the alkylene-joined ring system compounds of two or more aromatic rings joined by one or more alkylene groups, e.g., diphenylalkanes such as diphenylmethane or 2,2-diphenylpropane. The preferred aromatic ring system is a single aromatic ring and the preferred arylcyclobutene moiety is a benzocyclobutene moiety. The arylcyclobutene moiety is hydrocarbyl and is otherwise unsubstituted except for the carboxyl group in the 1-position or is substituted with inert groups such as cyano in other ring positions. The preferred arylcyclobutenecarboxylic acids are unsubstituted except for the carboxyl group and particularly preferred is 1-benzocyclobutenecarboxylic acid.

The 1-arylcyclobutenecarboxylic acids are known compounds or are produced by known methods. A general review of arylcyclobutene chemistry, particularly benzocyclobutene chemistry, is provided by Klundt, Chemical Reviews, Vol. 70, No. 4, pages 471–487 (1970) and by the references cited in the review article. By way of a specific illustration, 1-benzocyclobutenecarboxylic acid is produced by rearrangement of an α-diazaindanone.

The N-glycidyl compounds which serve as the precursors of the novel esters of the invention are compounds having up to 30 carbon atoms inclusive which characterized by the presence of at least one and preferably up to 4 amino nitrogen atoms and at least two glycidyl groups attached to the amino nitrogen atoms. The compounds are cyclic in character and are aromatic, cycloaliphatic, heterocyclic or mixtures thereof having up to 4 rings inclusive which are fused or are joined by direct valence bonds or by aliphatic, including cycloaliphatic, linking groups such as alkylene. The nitrogen atoms on which the glycidyl groups are substituted are present as amino groups including amide nitrogens and each valence of the nitrogen atom is substituted with a glycidyl group or is bound directly or indirectly through a functional group such as carbonyl or sulfonyl to a carbon atom forming part of a ring system. The N-glycidyl compound contains at least 2 and preferably up to 6 N-glycidyl groups and may contain other types of glycidyl groups such as glycidyl substituents. Compounds of these types having all rings as aromatic rings include 1,4-bis(diglycidylamino)benzene, bis[4-(diglycidylamino)phenyl]methane, 4,4'-(diglycidylamino)biphenyl, 4-glycidyloxy-N,N-diglycidylaniline, 2-(4-glycidyloxyphenyl)-2-(4-diglycidylaminophenyl)propane and N,N,N',N'-tetraglycidyl-4-aminosulfonilamide. Compounds all of whose rings are cycloaliphatic include 1,4-bis(diglycidylamino)cyclohexane and 1-diglycidylamino-4-glycidyloxycyclooctane. Compounds whose rings are wholely heterocyclic include 5,5-dimethyl-N,N'-diglycidylhydantoin and bis[3-(1-glycidylhydantoin)methane. Compounds containing rings of more than one type are illustrated by N,N'-diglycidyl-1,2,4,5-benzenetetracarboxylic acid diamide, di(N-glycidyl-3,4-maleimidophenyl) ketone and 4-diglycidylamino-1,2-[2,2,4-trimethyl-3-(4-diglycidylaminophenyl)cyclopentano]benzene. The preferred N-glycidyl compounds which serve as precursors of the novel esters of the invention are represented by the formula

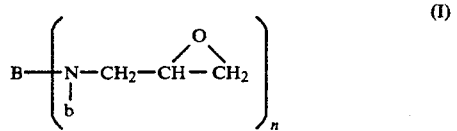

(I)

wherein B is a ring system of up to 4 rings which are aromatic, cycloaliphatic, heterocyclic or combinations thereof, which, when more than one ring is present are joined by direct valence bonds or aliphatic linking groups, and is hydrocarbyl except for carbonyl, sulfonyl or tertiary amino groups. The term b is glycidyl or a link to a carbon atom of B and n is 1 or 2. Of particular interest are the compounds of the above formula I of from 2 to 3 aromatic rings connected by alkylene linking groups and having a diglycidylamino substituent on each terminal ring. Of this latter class, bis(4-diglycidylaminophenyl)methane, 1,4-bis[2-(4-diglycidylaminophenyl)isopropyl]benzene and 1,4-bis[2-(4-diglycidylamino-3,5-dimethylphenyl)isopropyl]benzene are illustrative.

The novel esters of the invention are produced by reacting the 1-arylcyclobutenecarboxylic acid and the N-glycidyl compound in the liquid phase in the presence of a catalyst. Molar ratios of reactants sufficient to provide from about 0.5 mole to about 4 moles of 1-arylcyclobutenecarboxylic acid per mole of glycidyl group are satisfactory. However, the ester producing reaction requires 1 mole of 1-arylcyclobutenecarboxylic acid for each 1 mole of glycidyl group and quantities of reactants that are substantially stoichiometric are preferred.

The reaction is conducted in the substantial absence of reaction diluent when the reactants are liquid at reaction temperature or in the presence of an inert reaction diluent when part or all of the reaction mixture is solid at reaction temperature. Illustrative of suitable reaction diluents which are useful when diluents are employed are ethylbenzene and toluene. A satisfactory reaction rate is most easily accomplished if the 1-arylcyclobutenecarboxylic acid and the N-glycidyl compound are contacted in the presence of a catalyst. Quaternary phosphonium halides and quaternary ammonium halides have been found to be useful as catalyst, particularly tetra(hydrocarbyl)phosphonium halides wherein at least one of the hydrocarbyl moieties is phenyl with any other substituents being alkyl, particularly lower alkyl, and the halide is a middle halide, i.e., a chloride or a bromide. Illustrative of such phosphonium halides are trimethylphenylphosphonium chloride, ethyltriphenylphosphonium bromide, di-n-butyldiphenylphosphonium bromide and tetraphenylphosphonium chloride. Corresponding quaternary ammonium halides are also satisfactory. The alkyltriphenylphosphonium halides are preferred, especially ethyltriphenylphosphonium bromide. The phosphonium halide is employed in a catalytic quantity. Amounts of phosphonium halide from about 0.05% by weight to about 10% by weight, based on total reactants are satisfactory with amounts from about 0.5% by weight to about 6% by weight on the same basis being preferred.

The esterification reaction is conducted by mixing the 1-arylcyclobutenecarboxylic acid reactant and the N-glycidyl compound, the catalyst and any diluent to be employed and maintaining the resulting mixture under esterification conditions. An elevated temperature is generally utilized and reaction temperatures from about 30° C. to about 200° C. are satisfactory with reaction temperatures from about 50° C. to about 150° C. being preferred. The reaction pressure will be a pressure sufficient to maintain the reaction mixture in a liquid phase. Such pressures are typically up to 10 atmospheres but more often are from about 0.8 atmosphere to about 5 atmospheres. Subsequent to reaction the desired 1-arylcyclobutenecarboxylate ester is obtained from the product mixture. If desired, the ester product is separated and purified by conventional methods such as extraction, solvent removal or precipitation. Particularly in the embodiment where the reactants are provided in substantially stoichiometric quantities without added reaction diluent, the product is obtained in sufficiently high conversion and selectivity so as to allow its use in most applications without the need for purification.

The ester products of the invention are novel 1-arylcyclobutenecarboxylate esters of the N-glycidyl compound illustratively produced by the opening of the 3-membered ring of at least a portion of the glycidyl substituents with the resulting formation of a hydroxy group on the center carbon of each former glycidyl group and an ester linkage between the arylcyclobutene moiety and the terminal carbon atom of the former glycidyl group. Preferably, such a reaction to produce ester takes place at each glycidyl group of the N-glycidyl compound. Such reaction serves to produce an ester moiety of the formula

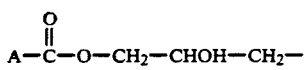

wherein A has the previously stated meaning, from at least a portion and preferably from all of the glycidyl groups present in the N-glycidyl compound. The ester products are therefore N-[3-(1-arylcyclobutenecarboxy)2-hydroxypropyl] derivatives of compounds of up to 30 carbon atoms having up to 4 rings which are fused or are joined by direct valence bonds or aliphatic linking groups, having at least one amino nitrogen atom and at least 1 and preferably from 2 to 6 of the N-[3-(1-arylcyclobutenecarboxy)-2-hydroxypropyl] groups as substituents or amino nitrogen atoms. In terms of the preferred N-glycidyl compounds of formula I, the ester products are represented by the formula

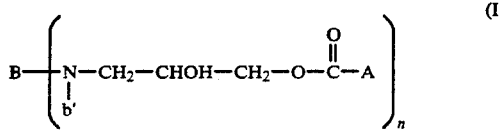

wherein B, A and n have the previously stated significance and b' is glycidyl, 3-(1-arylcyclobutenecarboxy)2-hydroxypropyl or a link to a carbon atom of B. The nomenclature of the ester products of the invention is rather complex. By way of a specific illustration, however, from the reaction of 1-benzocyclobutenecarboxylic acid and 1,4-bis(diglycidylamino)benzene is produced 1,4-bis[di(1-benzocyclobutenecarboxy-2-hydroxypropyl)amino]benzene. The identity of other products will be apparent from the above descriptions of and the formulas for the 1-arylcyclobutenecarboxylic acid and the N-glycidyl compound reactants.

The 1-arylcyclobutenecarboxylate esters of the invention are generally low melting solids. Although the esters will react easily with most conventional polyfunctional curing agents, e.g., cyanato or maleimido compounds and unsaturated compounds such as triallylisocyanurate, as well as with conventional catalytic curing agents both anionic and cationic, the esters are also self-curing and will cure or crosslink without the presence of added curing agent by heating the ester to a temperature above about 150° C. and preferably from about 175° C. to about 275° C. The cured products are rigid thermosets having a highly crosslinked structure and good properties of physical strength. The esters are processed by methods which are conventional for curing monomeric polymerizable compounds by application of heat. The cured products find utility as structural and coating materials in aerospace and electronic applications.

The invention is further illustrated by the following Illustrative Embodiments which should not be regarded as limiting the invention.

ILLUSTRATIVE EMBODIMENT I

A mixture of 6.56 g (0.01 mole) of 1,4-bis[2-(4-diglycidylaminophenyl)isopropyl]benzene, 5.92 g (0.04 mole) of 1-benzocyclobutenecarboxylic acid and 0.2 g of ethyltriphenylphosphonium bromide was warmed to 100° C.–105° C. and maintained at that temperature until no further reaction took place. The resulting product was obtained in a yield greater than 99%. The nuclear magnetic resonance spectra were consistent with the structure for N,N,N',N'-tetra[3-(1-benzocyclobutenecarboxy)-2-hydroxy-1-propyl]-1,4-bis[2-(4-aminophenylisopropyl]benzene.

ILLUSTRATIVE EMBODIMENT II

The tetra ester product of Illustrative Embodiment I was heated at 200° C. for two hours and at 220° C. for an additional two hours. The resulting product was a crosslinked, insoluble solid having a glass transition temperature of 125° C.

What is claimed is:
1. A 1-arylcyclobutenecarboxylate ester of a N-glycidyl compound wherein the arylcyclobutene moiety is benzocyclobutene and the N-glycidyl compound has up to 4 rings and up to 30 carbon atoms, inclusive, has from 1 to 4 amino nitrogens and from 2 to 6 glycidyl groups attached to amino nitrogen atoms.
2. The ester of claim 1 wherein, within the N-glycidyl compound, the rings are aromatic, cycloaliphatic, heterocyclic or mixtures thereof, connected by direct valence bonds or aliphatic linking groups, and each valence of each amino nitrogen is substituted with glycidyl or is bound directly or indirectly through carbonyl or sulfonyl to a carbon atom forming a part of a ring.
3. The ester of claim 2 wherein the N-glycidyl compound is represented by the formula

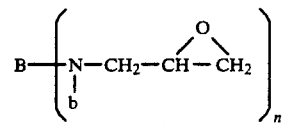

wherein B is a ring system of up to 4 rings and is hydrocarbyl except for carbonyl, sulfonyl or tertiary amino groups, b is glycidyl or a link to a carbon atom of B and n is 1 or 2.
4. The ester of claim 3 represented by the formula

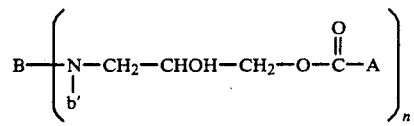

wherein b' is 3-(1-benzocyclobutenecarboxy)-2-hydroxypropyl and A is 1-benzocyclobutene.
5. The ester of claim 4 wherein n is 2.
6. The ester of claim 5 wherein B is

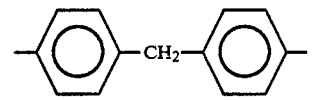

7. The ester of claim 5 wherein B is

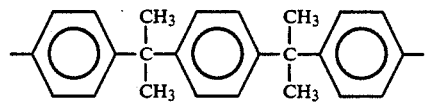

8. The ester of claim 5 wherein B is

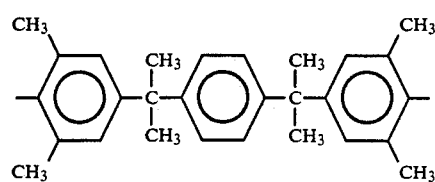

* * * * *